(12) United States Patent
Lin

(10) Patent No.: US 9,155,548 B2
(45) Date of Patent: Oct. 13, 2015

(54) POSITIONING DEVICE FOR BONE DRILLING

(71) Applicant: Hsieh-Hsing Lin, New Taipei (TW)

(72) Inventor: Hsieh-Hsing Lin, New Taipei (TW)

(*) Notice: Subject to any disclaimer, the term of this patent is extended or adjusted under 35 U.S.C. 154(b) by 249 days.

(21) Appl. No.: 13/797,059

(22) Filed: Mar. 12, 2013

(65) Prior Publication Data

US 2014/0276879 A1    Sep. 18, 2014

(51) Int. Cl.
*A61B 17/17* (2006.01)
*A61C 1/08* (2006.01)

(52) U.S. Cl.
CPC ............. *A61B 17/1757* (2013.01); *A61B 17/17* (2013.01); *A61C 1/084* (2013.01)

(58) Field of Classification Search
CPC ........ A61C 1/082; A61C 1/084; A61B 17/17; A61B 17/1757
USPC ................... 606/96–98; 433/75, 76
See application file for complete search history.

(56) References Cited

U.S. PATENT DOCUMENTS

| | | | | |
|---|---|---|---|---|
| 5,888,065 | A * | 3/1999 | Sussman | 433/76 |
| 7,322,821 | B1 | 1/2008 | Lin | |
| 7,845,943 | B2 * | 12/2010 | Meitner | 433/75 |
| 2007/0276401 | A1 * | 11/2007 | Choe et al. | 606/96 |
| 2010/0185201 | A1 * | 7/2010 | Kim | 606/80 |
| 2010/0297574 | A1 * | 11/2010 | Llop et al. | 433/75 |

* cited by examiner

*Primary Examiner* — David Bates
*Assistant Examiner* — Michael Araj
(74) *Attorney, Agent, or Firm* — Tracy M. Heims; Apex Juris, Pllc.

(57) ABSTRACT

The positioning device for bone drilling comprises a base, and the base has an outer wall, a positioning block, a guiding recess and an inner wall. The positioning block is formed on the outer wall of the base. The guiding recess is formed longitudinally through the base. The inner wall surrounds the guiding recess and the inner wall is a concave camber. The doctor can use the positioning block to fix the positioning device on a guide mold. A relative position between the positioning device and the guide mold can be relatively fixed. Prior to or during the drilling, the doctor can replace the positioning device with another positioning device with a more suitable diameter, oblique angle and oblique direction so that the positioning device for bone drilling can drill a hole at an accurate position, at an accurate oblique angle and in an accurate oblique direction as desired.

14 Claims, 12 Drawing Sheets

POSITIONING DEVICE FOR BONE DRILLING

BACKGROUND OF THE INVENTION

1. Field of the Invention

The present invention relates to a positioning device for bone drilling, and more particularly to a positioning device for bone drilling or implantation.

2. Description of Related Art

In a conventional surgery method, a doctor plans the position and path of inversion according to an X-ray image or a computerized tomography of a patient's bone, as well as relying on the doctor's anatomy knowledge and clinical surgery experience. As accuracy, safety and reliability of a surgery rely crucially on the clinical experience of the doctor, a less experienced doctor may not be able to fully control the quality of surgery. Selection of position and angle of a bone screw implant is crucial so as to avoid hurting a nerve and a vein of a patient during a surgery, otherwise the patient may suffer from sequelae such as hemiplegia.

For a dentist, when a patient's tooth is broken or missing, a normal treatment is to replace the tooth with a denture. A common method of a denture implant is fixed tooth implant. The fixed tooth implant is drilling a hole at an appropriate position where a tooth is missing on a gum bone in a patient's mouth, and then an artificial tooth root is implanted in the hole. The hole is sutured after implantation of the artificial tooth root. When the artificial tooth root grows fully integrated with the gum bone, a holder having a screw is mounted on the artificial tooth root. The denture is mounted around the holder and fully sustained on the gum bone by the holder and the artificial tooth root, so the denture can bear a bite force between the upper and down rows of teeth of the patient to restore a biting function of the patient's teeth.

Furthermore, depth, angle, position and size of the hole on the gum bone of the patient influence afterwards the depth and position of the implantation of the artificial tooth root on the gum bone of the patient, and even influence the biting between the denture and the patient's original teeth. In addition, a dentist must first drill a small hole on the gum bone of the patient, and then gradually enlarge the hole to prevent the gum bone of the patient from collapsing during drilling due to osteoporosis.

U.S. Pat. No. 7,322,821, which is incorporated herein as a reference, discloses a conventional positioning device for bone drilling and has a magnetic rod. An outer side of the magnetic rod attracts multiple semicircular guiding panels into stack by a magnetic force. A radius of curvature of each semicircular guiding panel gradually increases from the innermost guiding panel attached on the magnetic rod to the outermost guiding panel.

A dentist can simulate an angle and a diameter of the hole drilled on the position of the missing tooth on the gum bone of the patient by the conventional positioning devices based on a model of a gum of the patient, and accordingly make a guide mold mounted around the position of the missing tooth on the gum bone of the patient. The guide mold has a notch corresponding to the missing tooth in position to accommodate the conventional positioning devices. Drilling the hole on the gum bone of the patient includes the following steps.

First, the magnetic rod is removed, and then the dentist drills the hole with a drill having a rod diameter that equals the radius of curvature of the innermost guiding panel to drill downward on the position of the missing tooth on the gum bone of the patient through a preset angle of the innermost guiding panel.

Second, the innermost guiding panel is removed, and then the dentist drills the hole with a drill having a rod diameter that equals the radius of curvature of the next guiding panel to drill downward and enlarge the hole on the position of the missing tooth on the gum bone of the patient.

The dentist removes the guiding panels in sequence and uses the drills having different rod diameters to gradually enlarge the hole on the gum bone of the patient as desired.

However, the conventional positioning devices are simply placed in the notch of the guide mold without any design or mechanism to be fixed on the guide mold, so relative displacement between the conventional positioning devices and the guide mold frequently occurs. Consequently, the dentist cannot drill the hole at the accurate position, at the accurate oblique angle, and in the accurate direction as preset. In another aspect, the conventional positioning devices can be fixed by a fixing hole drilled on the magnetic rod and the guiding panels with a fixing part protruding into the fixing hole to fix a relative position between the magnetic rod and the guiding panels. However, when drilling a hole on a gum bone, sizes of the magnetic rod and the guiding panels are almost as large as a tooth, and the magnetic rod and the guiding panels thus have to be compactly designed. If the conventional positioning devices further include the fixing hole and the fixing part protruding in the fixing hole, a manufacture of the conventional positioning devices becomes highly complicated. Therefore, the conventional positioning devices still have to be improved.

SUMMARY OF THE INVENTION

The main objective of the invention is to provide a positioning device for bone drilling. The positioning device can mutually combine with and position a guide mold for simplified manufacture and easy operation.

The positioning device for bone drilling comprises a base, and the base has an outer wall, a positioning block, a guiding recess and an inner wall. The positioning block is formed on the outer wall of the base. The guiding recess is formed longitudinally through the base. The inner wall surrounds the guiding recess and the inner wall is a concave camber.

When using the positioning device, the doctor can use the positioning block to fix the positioning device on a guide mold. A relative position between the positioning device and the guide mold can be relatively fixed. During or prior to bone drilling, the doctor can replace the positioning device with another positioning device with a more suitable diameter, oblique angle, and oblique direction so that the positioning device for bone drilling of the present invention can drill a hole at an accurate position, at an accurate oblique angle, and in an accurate oblique direction as desired.

DETAILED DESCRIPTION OF THE PREFERRED EMBODIMENTS

Figure 1:
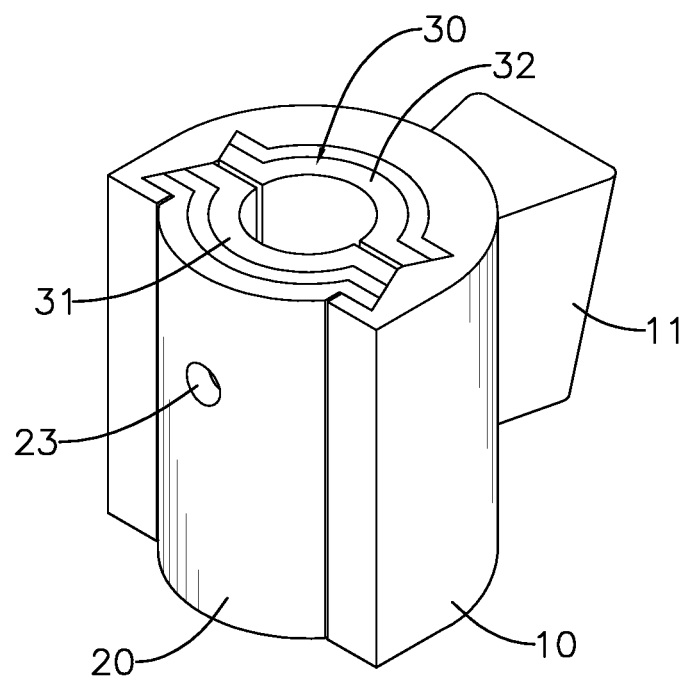
FIG. 1 is a perspective view of a first embodiment of a positioning device in accordance with the present invention.
Figure 2:
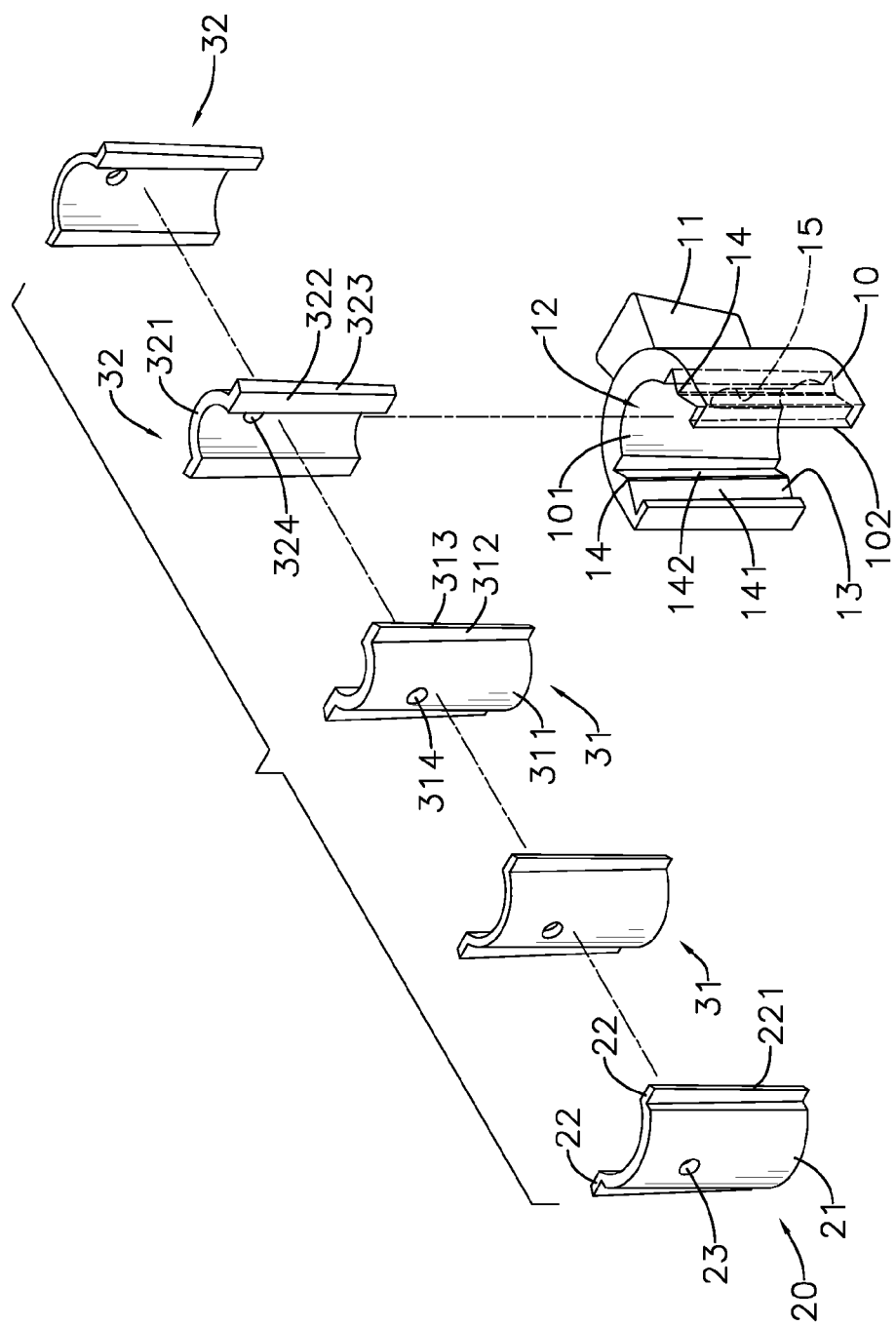
FIG. 2 is an exploded perspective view of the positioning device in FIG. 1.

In a preferred embodiment as shown in FIGS. 1 and 2, a positioning device in accordance with the present invention comprises a base 10, an outer guiding panel 20 and at least one inner guiding panel set 30.

The base 10 has a semicircular cross section and comprises an outer wall, a positioning block 11, a guiding recess 12, an inner wall 101, two positioning recesses 13, two guiding protrusions 14 and a hook recess 15. The positioning block 11 is formed on the outer wall of the base 10. The guiding recess 12 is formed longitudinally through the base 10 and is formed through the outer wall of the base 10 to form a side opening 102. The inner wall 101 of the base 10 surrounds the guiding recess 12 and is a concave camber. The positioning recesses 13 are formed separately on the inner wall 101 of the base 10, and the positioning recesses 13 are formed through the ends of the base 10 and are opposite to each other. The guiding protrusions 14 are each respectively formed on a wall of the positioning recesses 13. Each guiding protrusion 14 has an outer guide surface 141 and an inner guide surface 142. The outer guide surface 141 obliquely extends from the wall of the positioning recesses 13 in a direction away from the side opening 102 of the base 10. The inner guide surface 142 obliquely extends from the wall of the positioning recesses 13 in a direction toward the side opening 102 of the base 10. The hook recess 15 is formed on the inner wall 101, is formed longitudinally from a bottom of the base and is formed between the positioning recesses 13.

The outer guiding panel 20 is detachably mounted in the side opening 102 of the base 10 and has an arc body 21 and two ears 22. The arc body 21 of the outer guiding panel 20 is mounted inside and covers the side opening 102 of the base 10. The arc body 21 of the outer guiding panel 20 has a radius of curvature being equal to a radius of curvature of the inner wall 101 of the base 10. The arc body 21 of the outer guiding panel 20 has a hook hole 23. The ears 22 of the outer guiding panel 20 are respectively formed on opposite sides of the arc body 21 of the outer guiding panel 20 and are respectively mounted through the positioning recesses 13 of the base 10. The guiding recess 12 of the base 10 is surrounded by the inner wall 101 of the base 10 and the arc body 21 of the outer guiding panel 20. Each ear 22 of the outer guiding panel 20 has a side surface 221. A slope of the side surfaces 221 of the ears 22 of the outer guiding panel 20 corresponds to a slope of the outer guide surface 141 of the guiding protrusions 14. The side surfaces 221 of the ears 22 respectively abut the outer guide surfaces 141 of the guiding protrusions 14.

The at least one inner guiding panel set 30 is mounted through the guiding recess 12 of the base 10. Each one of the at least one inner guiding panel set 30 has a first inner guiding panel 31 and a second inner guiding panel 32.

The first inner guiding panel 31 is detachably mounted in the guiding recess 12 of the body 10 and has an arc body 311 and two ears 312. The arc body 311 of the first inner guiding panel 31 is semi-circular in cross-section and has a concave surface and a hook hole 314. The ears 312 are respectively formed on opposite sides of the arc body 311 of the first inner guiding panel 31, and are respectively mounted through the positioning recesses 13 of the base 10. Each ear 312 of the first inner guiding panel 31 has a side surface 313. A slope of the side surface 313 of the ears 312 of the first inner guiding panel 31 corresponds to a slope of the outer guide surface 141 of the guiding protrusions 14. The side surfaces 313 of the ears 312 respectively abut the outer guide surface 141 of the guiding protrusions 14.

The second inner guiding panel 32 is detachably mounted in the guiding recess 12 of the body 10, is attached symmetrically to the first inner guiding panel 31 to form a cylindrical cavity, and also has an arc body 321 and two ears 322. A radius of curvature of the arc body 321 equals the radius of curvature of the arc body 311 of the first inner guiding panel 31. The arc body 321 of the second inner guiding panel 32 is semi-circular in cross-section and has a concave surface and a hook hole 324. The concave surface of the arc body 321 of the second inner guiding panel 32 faces toward the concave surface of the arc body 311 of the first inner guiding panel 31, so as to form the cylindrical cavity. The ears 322 are respectively formed on opposite sides of the arc body 321 of the second inner guiding panel 32, and are respectively mounted through the positioning recesses 13 of the base 10. Each ear 322 of the second inner guiding panel 32 has a side surface 323. A slope of the side surface 323 of the ears 322 of the second inner guiding panel 32 corresponds to a slope of the inner guide surface 142 of the guiding protrusions 14. The side surfaces 323 of the ears 322 respectively abut the inner guide surface 142 of the guiding protrusions 14.

In a preferred embodiment, the positioning device for bone drilling as described has multiple inner guiding panel sets 30. The first inner guiding panels 31 of the multiple inner guiding panel sets 30 are stacked side by side into a row, the second inner guiding panels 32 of the multiple inner guiding panel sets 30 are stacked side by side into another row, and the innermost first inner guiding panels 31 is assembled with the innermost second inner guiding panels 32. The radius of curvature of each arc body 311 of the first inner guiding panels 31 and the radius of curvature of each arc body 321 of the second inner guiding panels 32 gradually increase from inside to outside. The arc body 311 of the outermost first inner guiding panel 31 abuts the arc body 21 of the outer guiding panel 20. The arc body 321 of the outermost second inner guiding panel 32 abuts the inner wall 101 of the base 10.

Figure 3:
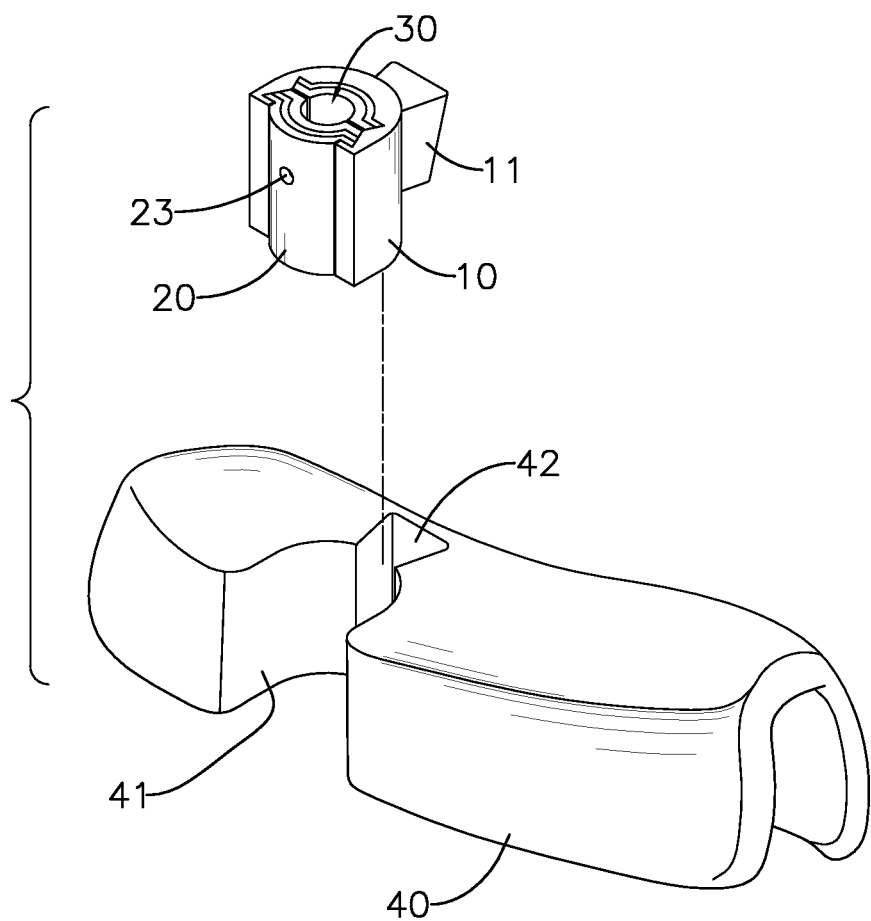
FIG. 3 is an operational perspective view of the positioning device in FIG. 1, shown combined with a guide mold.
Figure 6:
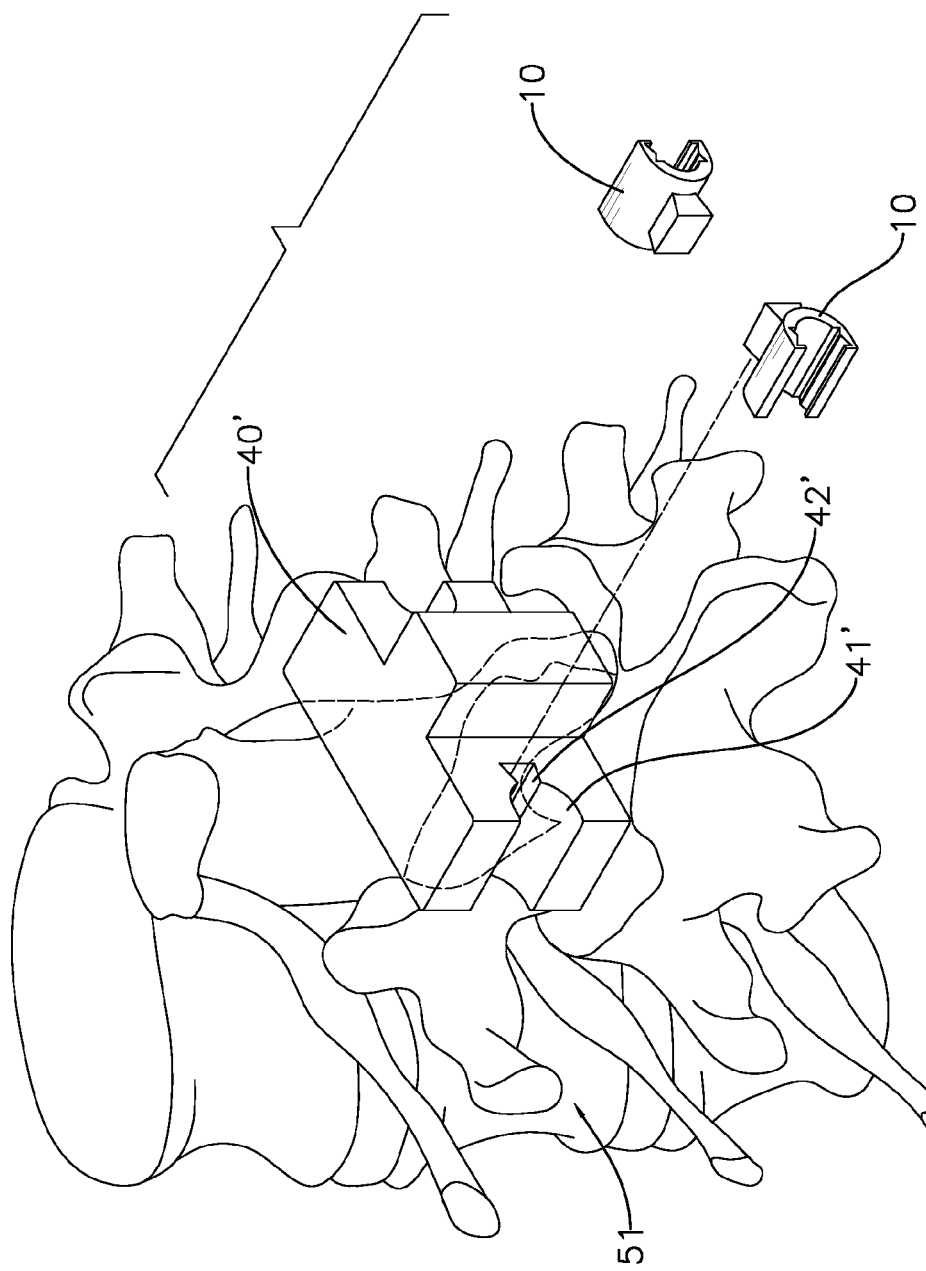
FIG. 6 is an operational top view of the positioning device in FIG. 1 with a guide mold, shown mounted around the vertebra of a patient.

With reference to FIGS. 3 and 6, the positioning device for bone drilling in accordance with the present invention is coordinated with a guide mold 40, 40'. A doctor uses computer simulation to create a simulation model of a hole to be drilled on an affected part of a patient so that the doctor can design the guide mold 40, 40' to be mounted on the affected part of the patient. Then the doctor designs specifications (such as size and oblique angle) of the guiding recess 12 of the base 10 in accordance with the simulation model of the hole. The doctor manufactures the real, physical guide mold 40, 40' by a solid forming machine, wherein the guide mold 40, 40' has a notch 41, 41' corresponding to the hole to be drilled on the affected part of the patient. The notch 41, 41' further comprises a positioning notch 42, 42'. The base 10 of the positioning device corresponds to a contour of the notch 41 and is mounted in the notch 41. The positioning block 11 of the base 10 is mounted through the positioning notch 42, 42' to fix the base 10 on the guide mold 40, 40', wherein a cross-section of the positioning block 11 of the base 10 and a cross-section of the positioning notch 42, 42' can be in a dovetail shape such that the positioning block 11 and the positioning notch 42, 42' corresponding to and engage with each other. A horizontal width of the positioning block 11 of the base 10 and a horizontal width of the positioning notch 42, 42' can be tapered from top to bottom such that the positioning block 11 and the notch 42, 42' gradually come into engagement with each other when the doctor is inserting the positioning block 11 into the positioning notch 42, 42'.

Figure 4:
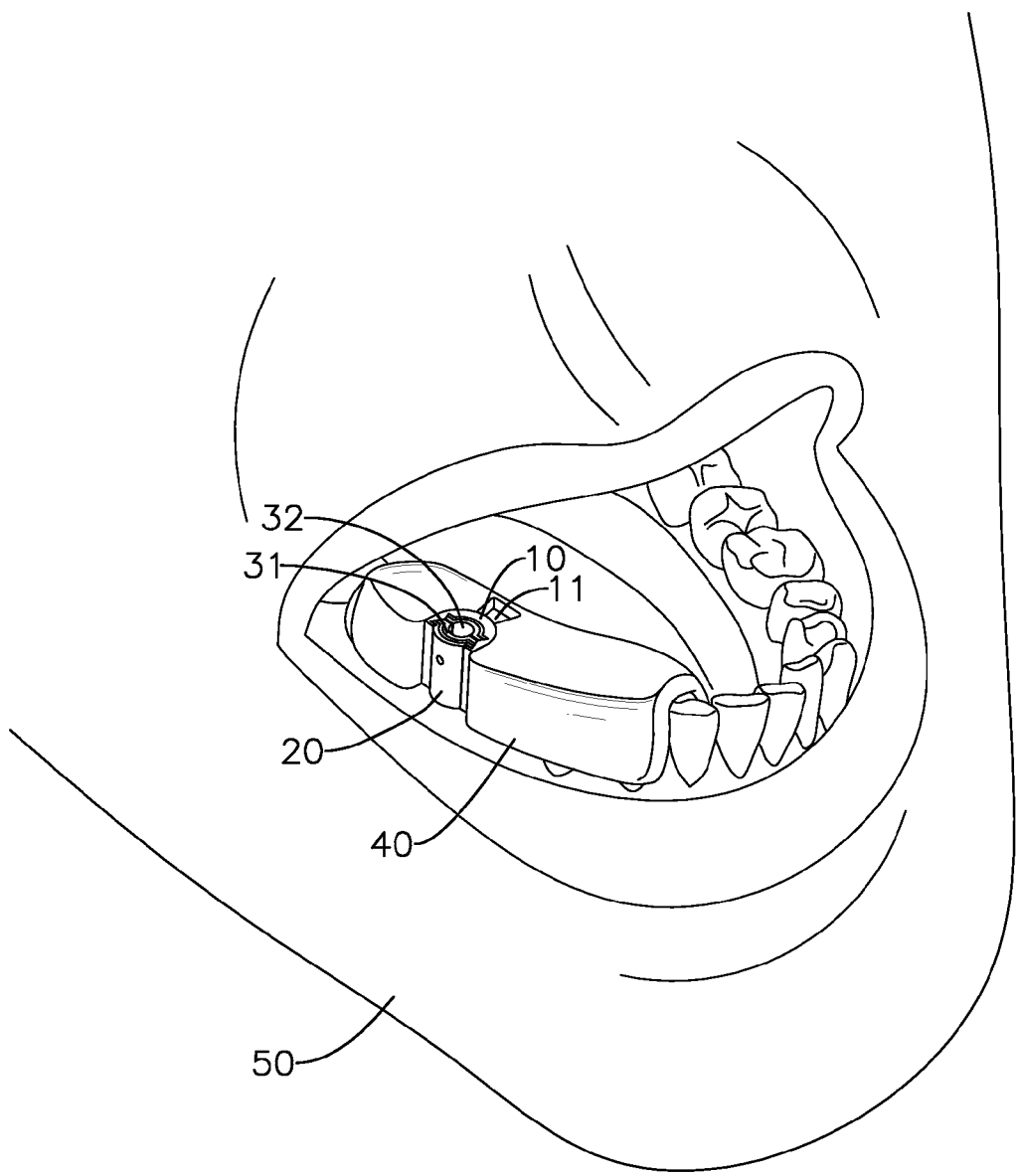
FIG. 4 is an operational perspective view of the positioning device in FIG. 1 with the guide mold, shown mounted around a tooth of a patient.
Figure 5:
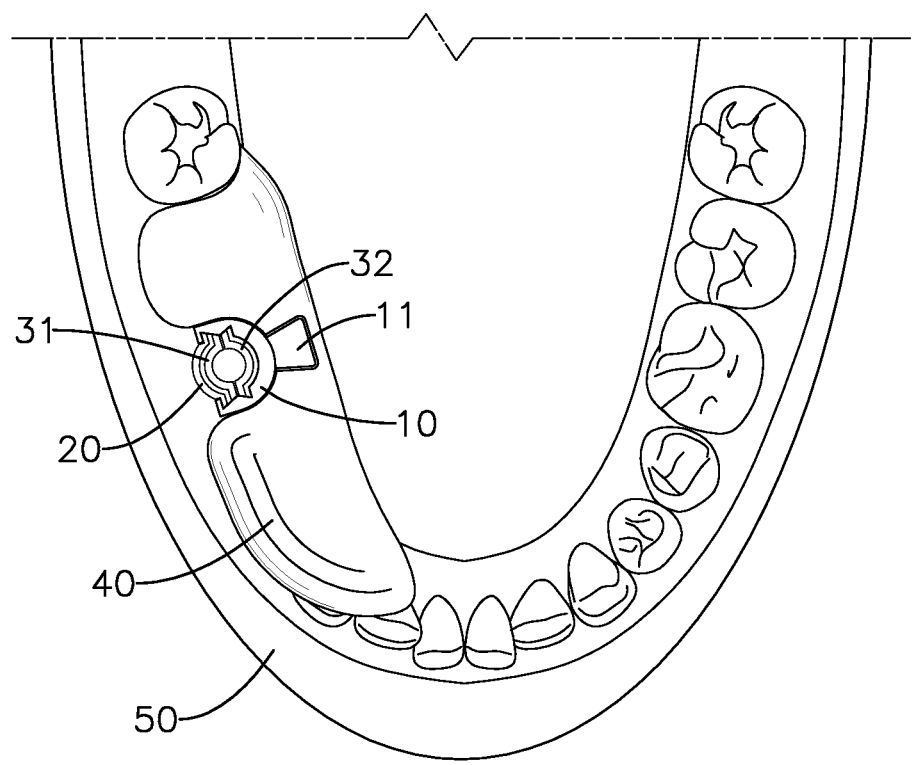
FIG. 5 is an operational top view of the positioning device in FIG. 1 with the guide mold, shown mounted around a tooth of a patient.

With reference to FIGS. 3 to 5, a dentist is drilling a hole on a position of a missing tooth on a gum bone of a patient 50. The guide mold 40 with the positioning device as described is mounted around teeth adjacent to the position of the missing tooth. The positioning device as described is mounted corresponding to the position of the missing tooth. The dentist drills the hole with a drill having a smaller rod diameter and corresponding to a radius of curvature of the first inner guiding panel 31 and a radius of curvature of the second inner guiding panel 32 of the innermost inner guiding panel set 30, and then removes the innermost inner guiding panel set 30 and enlarges the hole with another drill having a larger rod diameter and corresponding to a radius of curvature of the first inner guiding panel 31 and a radius of curvature of the second inner guiding panel 32 of the next inner guiding panel set 30 until the hole is enlarged to the extent as desired, wherein the dentist can remove or mount the outer guiding panel 20, the first inner guiding panel 31 and the second inner guiding panel 32 from the base 10 with a hook through the hook holes 23, 314, 324 respectively formed on the outer guiding panel 20, the first inner guiding panel 31 and the second inner guiding panel 32. The base 10 can also be removed from or mounted on the guide mold 40 with the hook through the hook recess 15 of the base 10.

With reference to FIG. 6, a doctor is drilling two holes on opposite sides of a vertebra 51 of the patient 50. The guide mold 40' with the positioning device as described is mounted on the vertebra 51. Two notches 41' are respectively formed on opposite sides of the guide mold 40', and two positioning notches 42' are respectively formed on opposite sides of the guide mold 40'. The notches 41' respectively correspond to the predetermined drilling positions on opposite sides of the vertebra 51. The doctor drills the holes as desired on the predetermined drilling positions on the vertebra 51 by the guide mold 40' with the positioning device of the present invention.

Figure 7:
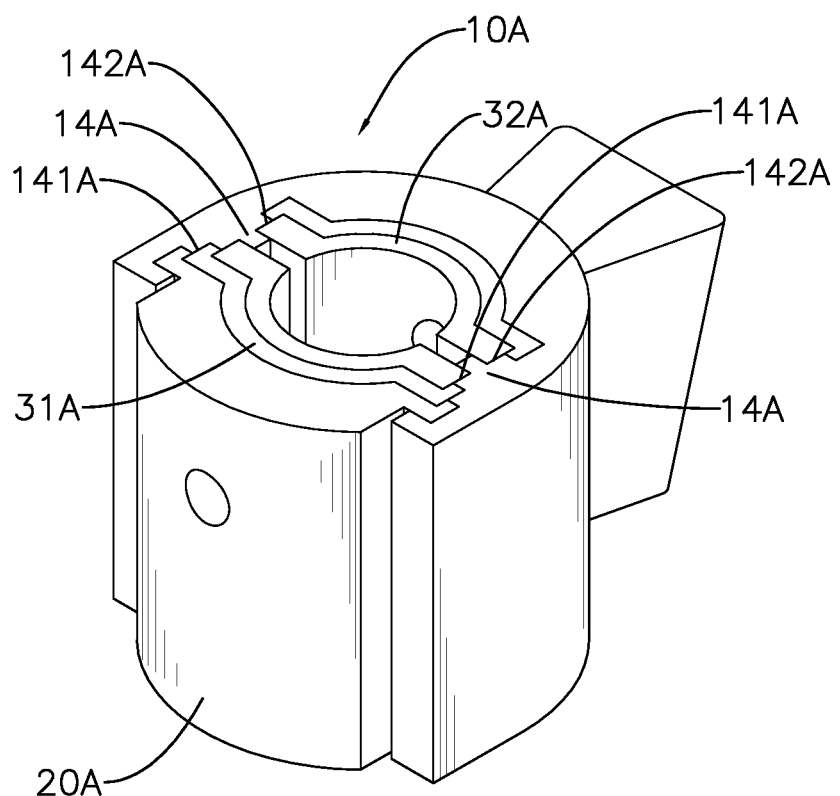
FIG. 7 is a perspective view of a second embodiment of a positioning device in accordance with the present invention.
Figure 8:
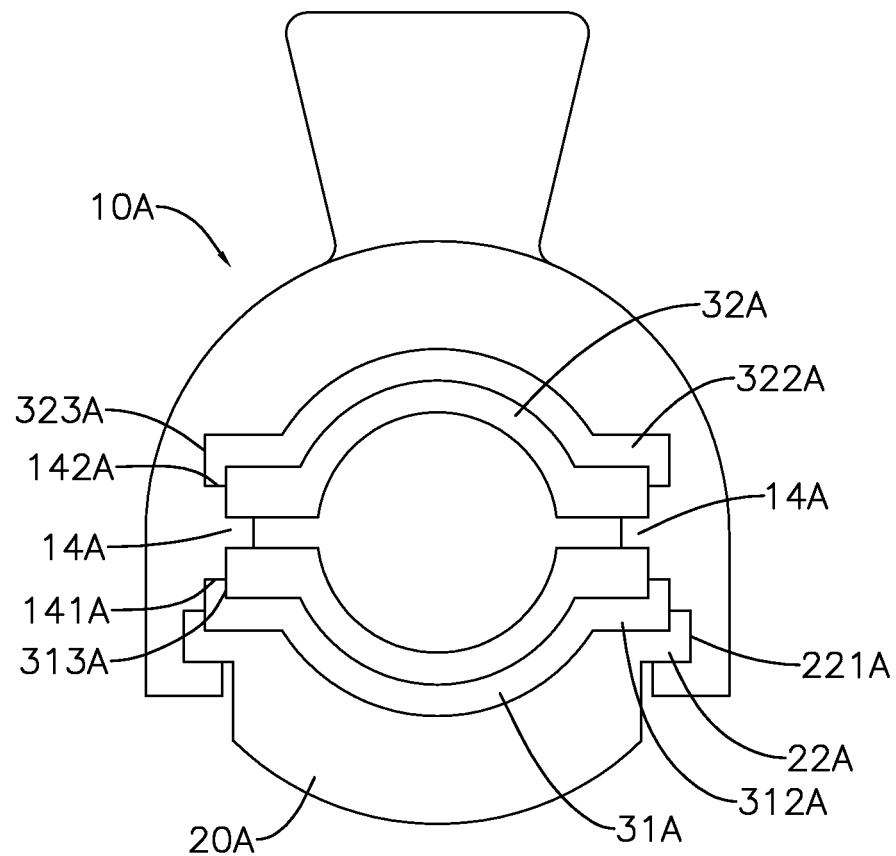
FIG. 8 is a top view of the positioning device in FIG. 7.

In another preferred embodiment as shown in FIGS. 7 and 8, the outer guide surface 141A and the inner guide surface 142A of the guiding protrusions 14A of the base 10A are both formed as stepped surfaces. The side surfaces 221A, 313A, 323A of the ears 22A, 312A, 322A of the outer guiding panel 20A, the first inner guiding panel 31A and the second inner guiding panel 32A each respectively abut the stepped outer guide surface 141A and the stepped inner guide surface 142A. The ears 312A, 322A of the first inner guiding panel 31A and the second inner guiding panel 32A are fixed between the first inner guiding panel 31A, the second inner guiding panel 32A or the outer guiding panel 20A abutting the guiding protrusions 14A.

Figure 9:
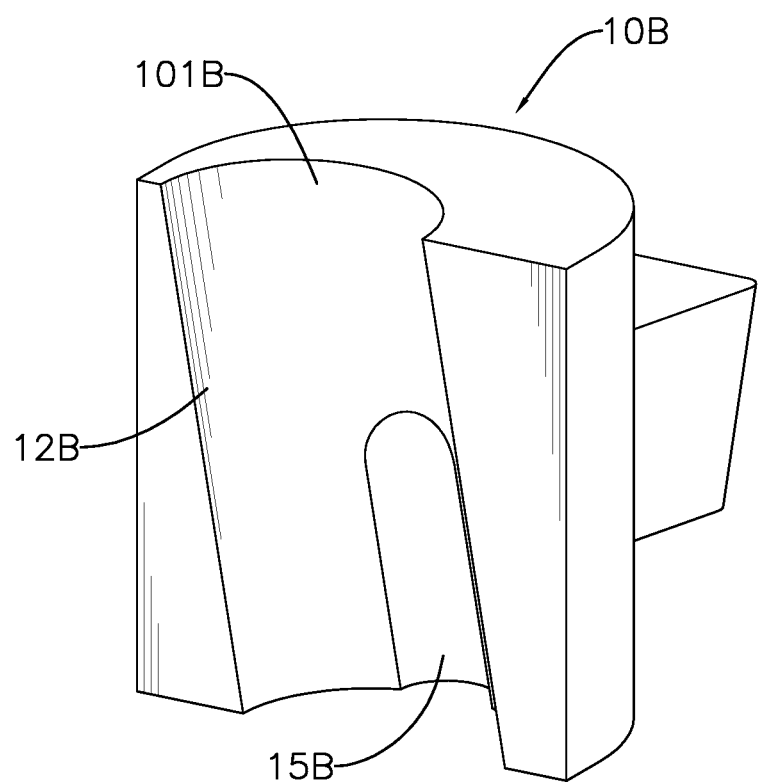
FIG. 9 is a perspective view of a third embodiment of a positioning device in accordance with the present invention.

In another preferred embodiment as shown in FIG. 9, wherein the base 10B does not have the positioning recess and the guiding protrusion as previously described. The guiding recess 12B is obliquely formed on the base 10B from top to bottom and from left to right. The inner wall 101B surrounds the guiding recess 12B and has a hook recess 15B.

Figure 10:
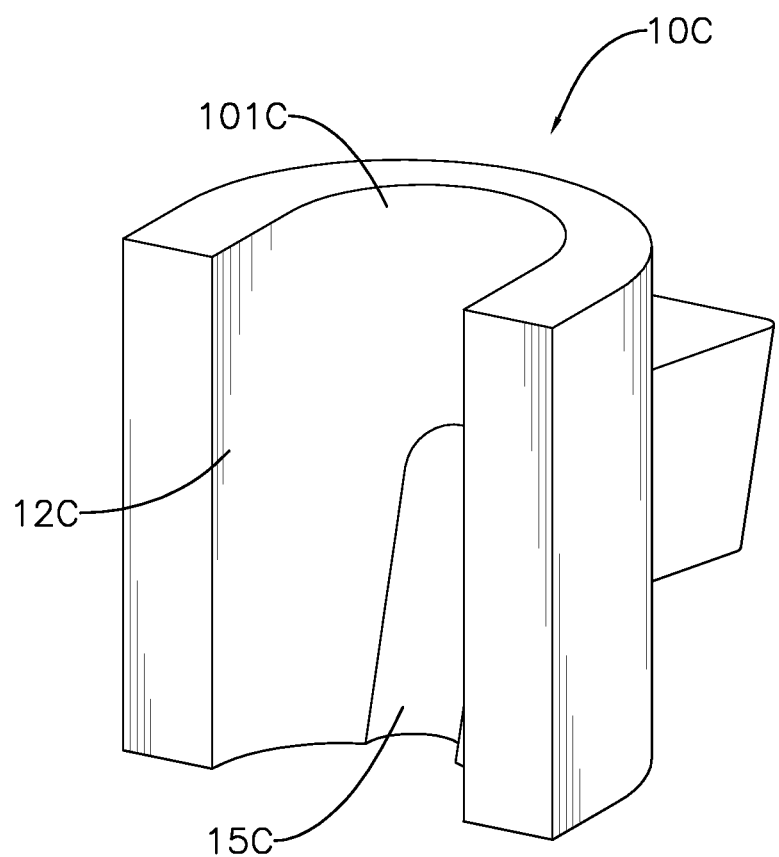
FIG. 10 is a perspective view of a fourth embodiment of a positioning device in accordance with the present invention.

In another preferred embodiment as shown in FIG. 10, wherein the base 10C does not have the positioning recess and the guiding protrusion as previously described. The guiding recess 12C is obliquely formed on the base 10C from top to bottom and from rear to front. The inner wall 101C surrounds the guiding recess 12C and has a hook recess 15C.

In the third and fourth preferred embodiments, the base 10B, 10C can be independently mounted on the guide mold 40, 40' when only one round of drilling is to be performed.

The doctor mounts the outer guiding panel 20 and the at least one inner guiding panel set 30 on the base 10, 10A, and then uses the positioning block 11 of the base 10, 10A, 10B, 10C to fix the positioning device as described on the guide mold 40, 40'. A relative position between the present invention and the guide mold 40, 40' can be relatively fixed and the outer guiding panel 20 and the at least one inner guiding panel set 30 do not move arbitrarily. Prior to or during drilling, the doctor can replace the positioning device with another positioning device with a more suitable diameter, oblique angle, and oblique direction such that the positioning device for bone drilling of the present invention can drill a hole at an accurate position, at an accurate oblique angle, and in an accurate oblique direction as desired according to the particular situation of the patient 50.

Figure 11:
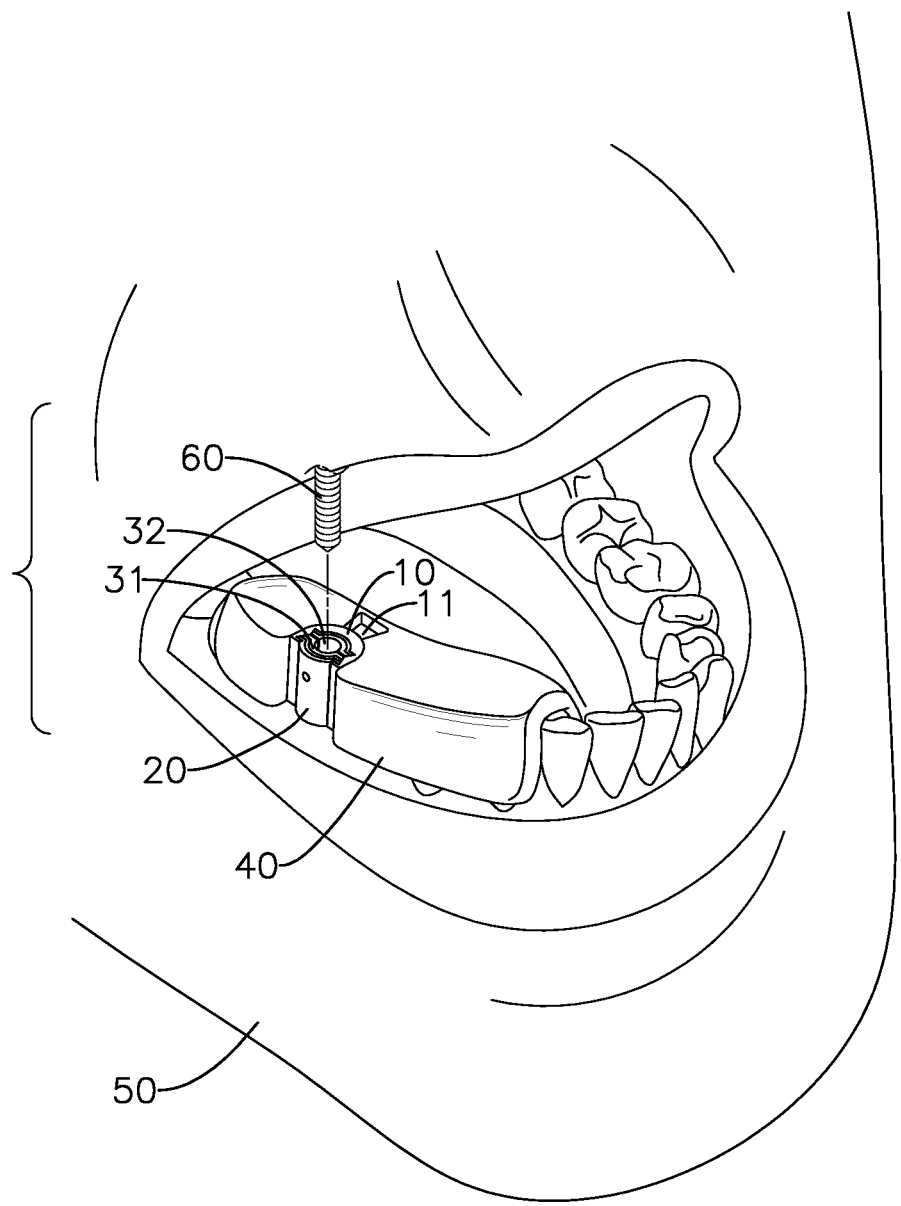
FIG. 11 is an operational perspective view of the positioning device in FIG. 1 with the guide mold, shown drilling a tooth of a patient in axial direction.
Figure 12:
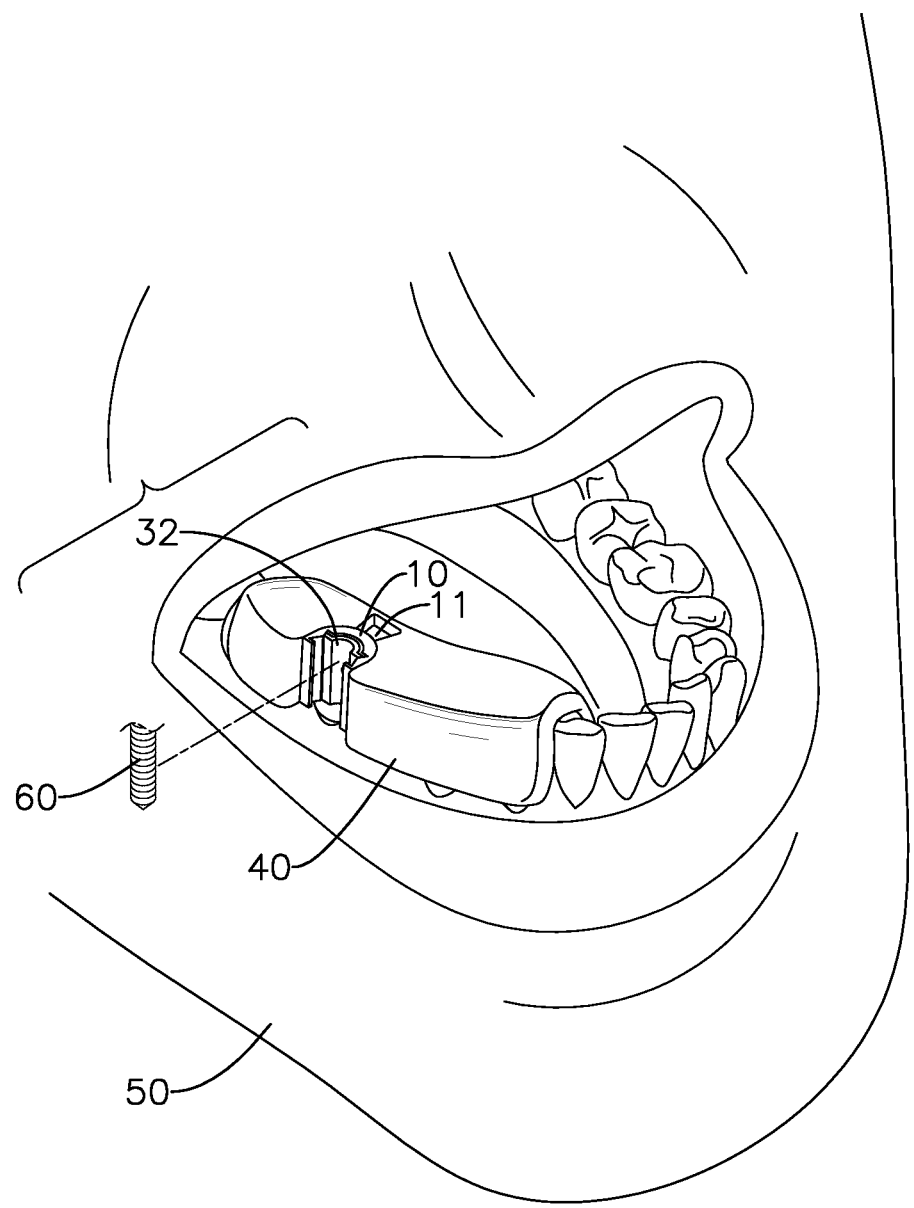
FIG. 12 is an operational perspective view of the positioning device in FIG. 1 with the guide mold, shown drilling a tooth of a patient in radial direction.

With reference to FIGS. 11 and 12, when the doctor uses the positioning device as described having the outer guiding panel 20, and the first inner guiding panel 31, a cylindrical space is formed in the base 10 to fix a moving direction of a drill 60 to avoid an offset during drilling. In addition, the positioning device as described can also be used without the outer guiding panel 20 and the first inner guiding panel 31 to form a semi-columnar space having a side opening, such that the doctor can insert the drill 60 into the base 10 from a side of the base 10 as shown in FIG. 12, and finely adjust a direction and an angle of the drill 60 according to the doctor's expertise and the particular situation of the patient.

In addition, in a preferred embodiment, material of a positioning device in accordance with the present invention includes metal, ceramic, plastic, glass, resin or componomer.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:
1. A positioning device for bone drilling comprising:
   a base comprising
      an outer wall;
      a positioning block formed on the outer wall of the base;
      a guiding recess formed longitudinally through the base and formed longitudinally through the outer wall of the base to form a side opening; and
      an inner wall surrounding the guiding recess, and the inner wall being a concave camber; and
      two positioning recesses formed apart on the inner wall of the base, and the positioning recesses oppositely formed through the base;
   an outer guiding panel detachably mounted in the side opening and comprising an arc body mounted inside the side opening of the base, the arc body being a plate with an arc section, and a radius of curvature of the arc body being equal to a radius of curvature of the inner wall of the base; and two ears respectively formed on opposite sides of the arc body of the outer guiding panel, and respectively mounted through the positioning recesses of the base;

wherein the arc body of the outer guiding panel covers the side opening of the base, and the guiding recess of the base is surrounded by the inner wall of the base and the arc body of the outer guiding panel; and at least one inner guiding panel set mounted through the guiding recess of the base, and each one of the at least one inner guiding panel set comprising a first inner guiding panel detachably mounted in the guiding recess of the base and comprising an arc body having a semicircular cross section and a concave surface; and two ears respectively formed on opposite sides of the arc body of the first inner guiding panel, and respectively mounted through the positioning recesses of the base; and a second inner guiding panel detachably mounted in the guiding recess of the base and comprising an arc body having a semicircular cross section and a concave surface, the concave surface of the arc body of the second inner guiding panel facing toward the concave surface of the arc body of the first inner guiding panel to form a cylindrical cavity; and two ears respectively formed on opposite sides of the arc body of the second inner guiding panel, and respectively mounted through the positioning recesses of the base.

2. The positioning device for bone drilling as claimed in claim 1, wherein the guiding recess of the base is formed obliquely.

3. The positioning device for bone drilling as claimed in claim 2, wherein the inner wall of the base further comprises a hook recess;

wherein the arc body of the outer guiding panel further comprises a hook hole;

wherein the arc body of the first inner guiding panel further comprises a hook hole; and wherein the arc body of the second inner guiding panel further comprises a hook hole.

4. The positioning device for bone drilling as claimed in claim 2, comprising multiple inner guiding panel sets, wherein the first inner guiding panels of the multiple inner guiding panel sets are stacked side by side into a row, the second inner guiding panels of the multiple inner guiding panel sets are stacked side by side into another row, and then the innermost first inner guiding panels are assembled with the innermost second inner guiding panels, wherein radiuses of curvature of each arc body of the first inner guiding panel and radiuses of curvature of each arc body of the second inner guiding panel gradually increase from inside to outside, the arc body of the outermost first inner guiding panel abuts the arc body of the outer guiding panel, and the arc body of the second inner guiding panel abuts the inner wall of the base.

5. The positioning device for bone drilling as claimed in claim 4, wherein the base further comprises two guiding protrusions respectively formed on a wall of the positioning recesses, and each guiding protrusion comprising an outer guide surface obliquely extending from the wall of the positioning recesses in a direction away from the side opening of the base; and an inner guide surface obliquely extending from the wall of the positioning recesses in a direction toward the side opening of the base;

wherein each ear of the outer guiding panel, the first inner guiding panel and the second inner guiding panel has a side surface, a slope of the side surface of the ears of the outer guiding panel and a slope of the side surface of the ears of the first inner guiding panel correspond to a slope of the outer guide surface of the guiding protrusions, and the side surfaces of the ears of the outer guiding panel and the first inner guiding panel abut the outer guide surface of the guiding protrusions; a slope of the side surface of the ears of the second inner guiding panel corresponds to a slope of the inner guide surface of the guiding protrusions, and the side surfaces of the ears of the second inner guiding panel abut the inner guide surface of the guiding protrusions.

6. The positioning device for bone drilling as claimed in claim 5, wherein the outer guide surface and the inner guide surface of the guiding protrusions of the base are formed as stepped surfaces.

7. The positioning device for bone drilling as claimed in claim 2, wherein the base further comprises two guiding protrusions respectively formed on a wall of the positioning recesses, and each guiding protrusion comprising an outer guide surface obliquely extending from the wall of the positioning recesses in a direction away from the side opening of the base; and an inner guide surface obliquely extending from the wall of the positioning recesses in a direction toward the side opening of the base;

wherein each ear of the outer guiding panel, the first inner guiding panel and the second inner guiding panel has a side surface, a slope of the side surface of the ears of the outer guiding panel and a slope of the side surface of the ears of the first inner guiding panel correspond to a slope of the outer guide surface of the guiding protrusions, and the side surfaces of the ears of the outer guiding panel and the first inner guiding panel abut the outer guide surface of the guiding protrusions; a slope of the side surface of the ears of the second inner guiding panel corresponds to a slope of the inner guide surface of the guiding protrusions, and the side surfaces of the ears of the second inner guiding panel abut the inner guide surface of the guiding protrusions.

8. The positioning device for bone drilling as claimed in claim 7, wherein the outer guide surface and the inner guide surface of the guiding protrusions of the base are formed as stepped surfaces.

9. The positioning device for bone drilling as claimed in claim 1, wherein the inner wall of the base further comprises a hook recess;

wherein the arc body of the outer guiding panel further comprises a hook hole;

wherein the arc body of the first inner guiding panel further comprises a hook hole; and wherein the arc body of the second inner guiding panel further comprises a hook hole.

10. The positioning device for bone drilling as claimed in claim 1, comprising multiple inner guiding panel sets, wherein the first inner guiding panels of the multiple inner guiding panel sets are stacked side by side into a row, the second inner guiding panels of the multiple inner guiding panel sets are stacked side by side into another row, and then the innermost first inner guiding panels are assembled with the innermost second inner guiding panels, wherein radiuses of curvature of each arc body of the first inner guiding panel and radiuses of curvature of each arc body of the second inner guiding panel gradually increase from inside to outside, the arc body of the outermost first inner guiding panel abuts the arc body of the outer guiding panel, and the arc body of the second inner guiding panel abuts the inner wall of the base.

11. The positioning device for bone drilling as claimed in claim 10, wherein the base further comprises
two guiding protrusions respectively formed on a wall of the positioning recesses, and each guiding protrusion comprising
an outer guide surface obliquely extending from the wall of the positioning recesses in a direction away from the side opening of the base; and
an inner guide surface obliquely extending from the wall of the positioning recesses in a direction toward the side opening of the base;
wherein each ear of the outer guiding panel, the first inner guiding panel and the second inner guiding panel has a side surface, a slope of the side surface of the ears of the outer guiding panel and a slope of the side surface of the ears of the first inner guiding panel correspond to a slope of the outer guide surface of the guiding protrusions, and the side surfaces of the ears of the outer guiding panel and the first inner guiding panel abut the outer guide surface of the guiding protrusions; a slope of the side surface of the ears of the second inner guiding panel corresponds to a slope of the inner guide surface of the guiding protrusions, and the side surfaces of the ears of the second inner guiding panel abut the inner guide surface of the guiding protrusions.

12. The positioning device for bone drilling as claimed in claim 11, wherein the outer guide surface and the inner guide surface of the guiding protrusions of the base are formed as stepped surfaces.

13. The positioning device for bone drilling as claimed in claim 1, wherein the base further comprises
two guiding protrusions respectively formed on a wall of the positioning recesses, and each guiding protrusion comprising
an outer guide surface obliquely extending from the wall of the positioning recesses in a direction away from the side opening of the base; and
an inner guide surface obliquely extending from the wall of the positioning recesses in a direction toward the side opening of the base;
wherein each ear of the outer guiding panel, the first inner guiding panel and the second inner guiding panel has a side surface, a slope of the side surface of the ears of the outer guiding panel and a slope of the side surface of the ears of the first inner guiding panel correspond to a slope of the outer guide surface of the guiding protrusions, and the side surfaces of the ears of the outer guiding panel and the first inner guiding panel abut the outer guide surface of the guiding protrusions; a slope of the side surface of the ears of the second inner guiding panel corresponds to a slope of the inner guide surface of the guiding protrusions, and the side surfaces of the ears of the second inner guiding panel abut the inner guide surface of the guiding protrusions.

14. The positioning device for bone drilling as claimed in claim 13, wherein the outer guide surface and the inner guide surface of the guiding protrusions of the base are formed as stepped surfaces.

* * * * *